(12) United States Patent
Chen et al.

(10) Patent No.: US 8,181,302 B2
(45) Date of Patent: May 22, 2012

(54) BRUSH ALIGNMENT CONTROL MECHANISM

(75) Inventors: Hung Chih Chen, Sunnyvale, CA (US); Hui Chen, Burlingame, CA (US); Dan Zhang, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 37 days.

(21) Appl. No.: 12/564,254

(22) Filed: Sep. 22, 2009

(65) Prior Publication Data

US 2011/0067727 A1   Mar. 24, 2011

(51) Int. Cl.
*A46B 13/00* (2006.01)
(52) U.S. Cl. ................ 15/77; 15/88.3; 15/102
(58) Field of Classification Search .... 15/77, 88.2–88.4, 15/102
See application file for complete search history.

(56) References Cited

U.S. PATENT DOCUMENTS

| | | | |
|---|---|---|---|
| 6,070,284 A * | 6/2000 | Garcia et al. ............ | 15/102 |
| 6,119,708 A | 9/2000 | Fishkin et al. | |
| 6,299,698 B1 | 10/2001 | Emami et al. | |
| 6,516,816 B1 | 2/2003 | Husain et al. | |
| 6,985,185 B1 | 1/2006 | Crawford et al. | |
| 6,986,185 B2 | 1/2006 | Sugarman et al. | |
| 7,229,504 B2 | 6/2007 | Sugarman et al. | |
| 7,377,002 B2 | 5/2008 | Yudovsky et al. | |
| 2003/0200988 A1 | 10/2003 | Brown et al. | |
| 2005/0109371 A1 | 5/2005 | Sin et al. | |
| 2005/0211276 A1 | 9/2005 | Yudovsky et al. | |
| 2005/0268937 A1 | 12/2005 | Sugarman | |
| 2007/0209135 A1 | 9/2007 | Chen et al. | |
| 2007/0221249 A1 | 9/2007 | Sugarman et al. | |

* cited by examiner

*Primary Examiner* — Shay Karls
(74) *Attorney, Agent, or Firm* — Patterson & Sheridan, LLP

(57) ABSTRACT

A method and apparatus for providing uniform pressure, friction and/or contact between a substrate and a cylindrical roller in a brush-type cleaning system is described. The apparatus includes an alignment member adapted to allow pivotal movement of the cylindrical roller based on the topography of a substrate and/or the outer surface of the cylindrical roller. The method includes positioning a substrate between two cylindrical rollers, moving each of the two cylindrical rollers to a position where at least a portion of an outer surface of each of the cylindrical rollers are in contact with the major surfaces of the substrate, and rotating one or both of the substrate and the two cylindrical rollers relative to each other while allowing a longitudinal axis of one or both of the two cylindrical rollers to pivot relative to a plane defined by one of the major surfaces of the substrate.

17 Claims, 8 Drawing Sheets

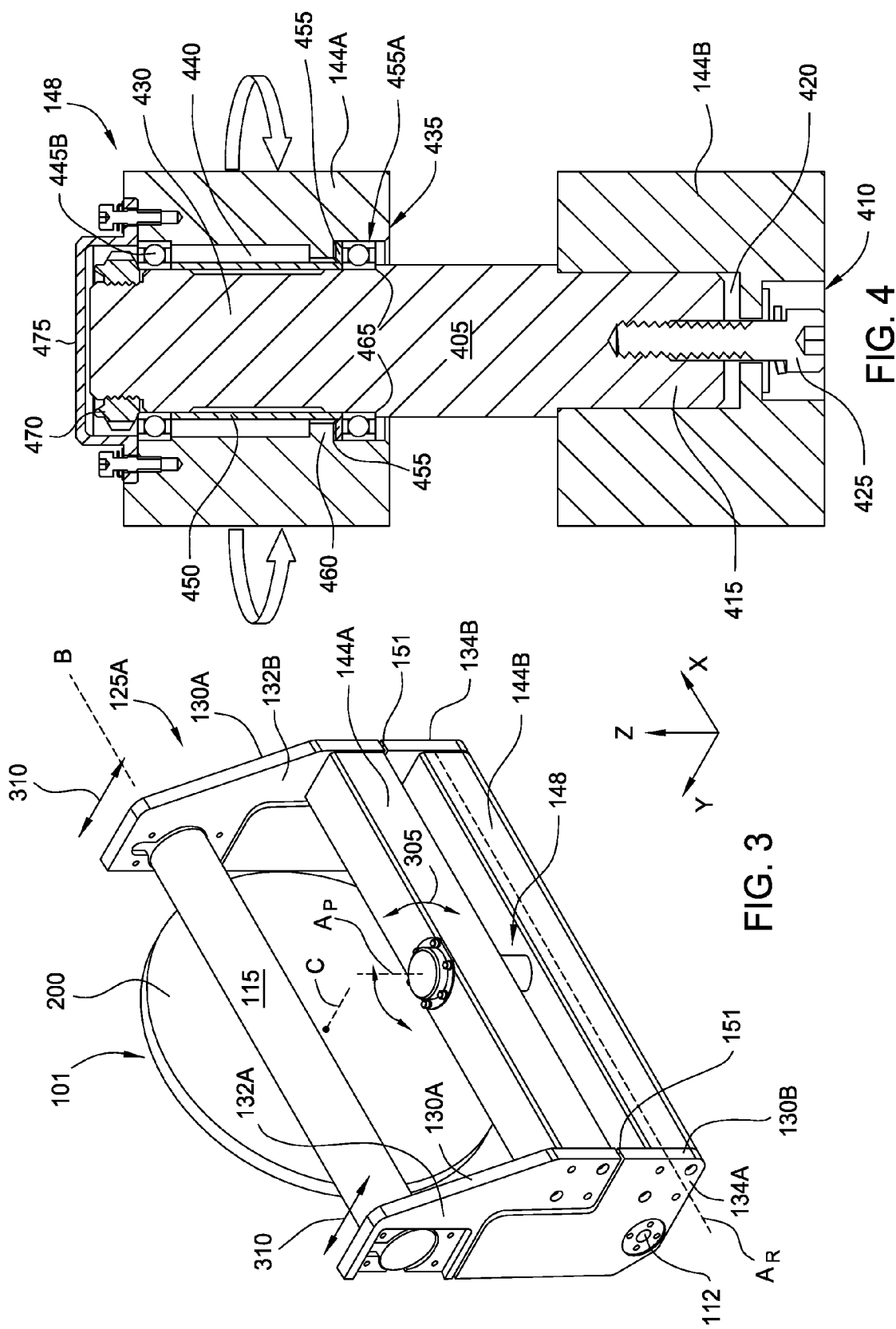

BRUSH ALIGNMENT CONTROL MECHANISM

BACKGROUND OF THE INVENTION

1. Field of the Invention

Embodiments of the present invention generally relate to an apparatus and a method for processing semiconductor substrates. More particularly, embodiments of the present invention provide apparatus and method for cleaning semiconductor substrates.

2. Description of the Related Art

During fabrication of a semiconductor device, various layers, such as oxides and metals, require planarization prior to depositing subsequent layers thereon. The planarization process can be followed by a cleaning process which removes residual polishing fluids and/or particles from polishing. Conventional cleaning processes generally include scrubbing the substrate surfaces with brushes made from a porous or sponge-like materials or bristles. The brushes are generally pressed against major surfaces of the substrate and rotated relative to the substrate. However, the brushes can be mishandled during installation which may cause the brush to become out of round. An out of round condition may undesirably cause uneven contact with the substrate as the brush is rotated against the substrate, which may detrimentally affect cleaning of the substrate and/or damage the substrate.

Therefore, there is a need for apparatus and method to ensure constant pressure of the brush against the substrate, ensure constant friction between the brush and the substrate, as well as maximize the brush contact with the substrate surface during rotation of the brush.

SUMMARY OF THE INVENTION

The present invention generally relates to a method and apparatus for processing a substrate using cylindrical rollers, wherein the rollers are controlled to consistently contact and/or apply consistent pressure and/or generate consistent friction against the substrate.

In one embodiment, a brush box for processing a semiconductor substrate is described. The brush box includes a base, a tank disposed on the base, and a pair of bracket assemblies disposed on opposing sides of the tank and movably coupled to the base. At least one of the bracket assemblies comprises a first bracket section having a first side and a second side separated by a first structural support member, and a second bracket section having a first side and a second side separated by a second structural support member, first bracket section being fixed to the second bracket section for lateral movement of the respective bracket assembly relative to the enclosure, and the first bracket section being pivotally movable relative to the second bracket section.

In another embodiment, a brush box for processing a semiconductor substrate is described. The brush box includes a base, a tank disposed on the base, and a pair of bracket assemblies disposed on opposing sides of the base and being coupled to an actuator providing movement of each bracket assembly in a rotational axis relative to the enclosure, at least one of the bracket assemblies comprising a first bracket section hingedly coupled to the base, and a second bracket section having a cylindrical roller coupled thereto, the second bracket section being fixed to the first bracket section for movement with the first bracket section on the rotational axis, and the second bracket section being movable in a pivotal axis relative to the first bracket section.

In another embodiment, a method for processing a substrate is described. The method includes positioning a substrate in a tank between two cylindrical rollers, moving each of the two cylindrical rollers to a position where at least a portion of an outer surface of each of the cylindrical rollers are in contact with major surfaces of the substrate, and rotating the substrate in a first rotational axis while rotating the two cylindrical rollers in a second rotational axis and a third rotational axis, wherein the second and third rotational axes are substantially parallel, the first rotational axis being substantially perpendicular to the second and third rotational axes, while allowing the orientation of one or both of the two cylindrical rollers to pivot in a fourth rotational axis relative to a plane defined by at least one of the major surfaces of the substrate.

BRIEF DESCRIPTION OF THE DRAWINGS

So that the manner in which the above-recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 3 is an isometric view of one embodiment of a bracket assembly that may be utilized in the brush box of FIGS. 1-2B.

FIG. 4 is a cross-sectional view of one embodiment of an alignment member that may be utilized in the bracket assembly of FIG. 3.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments described herein generally provide an apparatus and method for providing uniform pressure, friction and/or contact between a substrate and a cylindrical roller in a brush-type cleaning system that is utilized in a brush box. Embodiments of brush box that may be adapted to benefit from the invention include a cleaning module that is part of a REFLEXION® GT polishing system, available from Applied Materials, Inc., located in Santa Clara, Calif. Embodiments described herein may also be utilized on brush-type cleaning and polishing systems available from other manufacturers. While the embodiments of the cylindrical rollers described herein are exemplarily described as a media for cleaning substrates, some embodiments may be utilized for polishing substrates in a chemical mechanical polishing (CMP) system. For example, the cylindrical rollers may be made of or fitted with a pad material adapted to remove material from the substrate.

Figure 1:
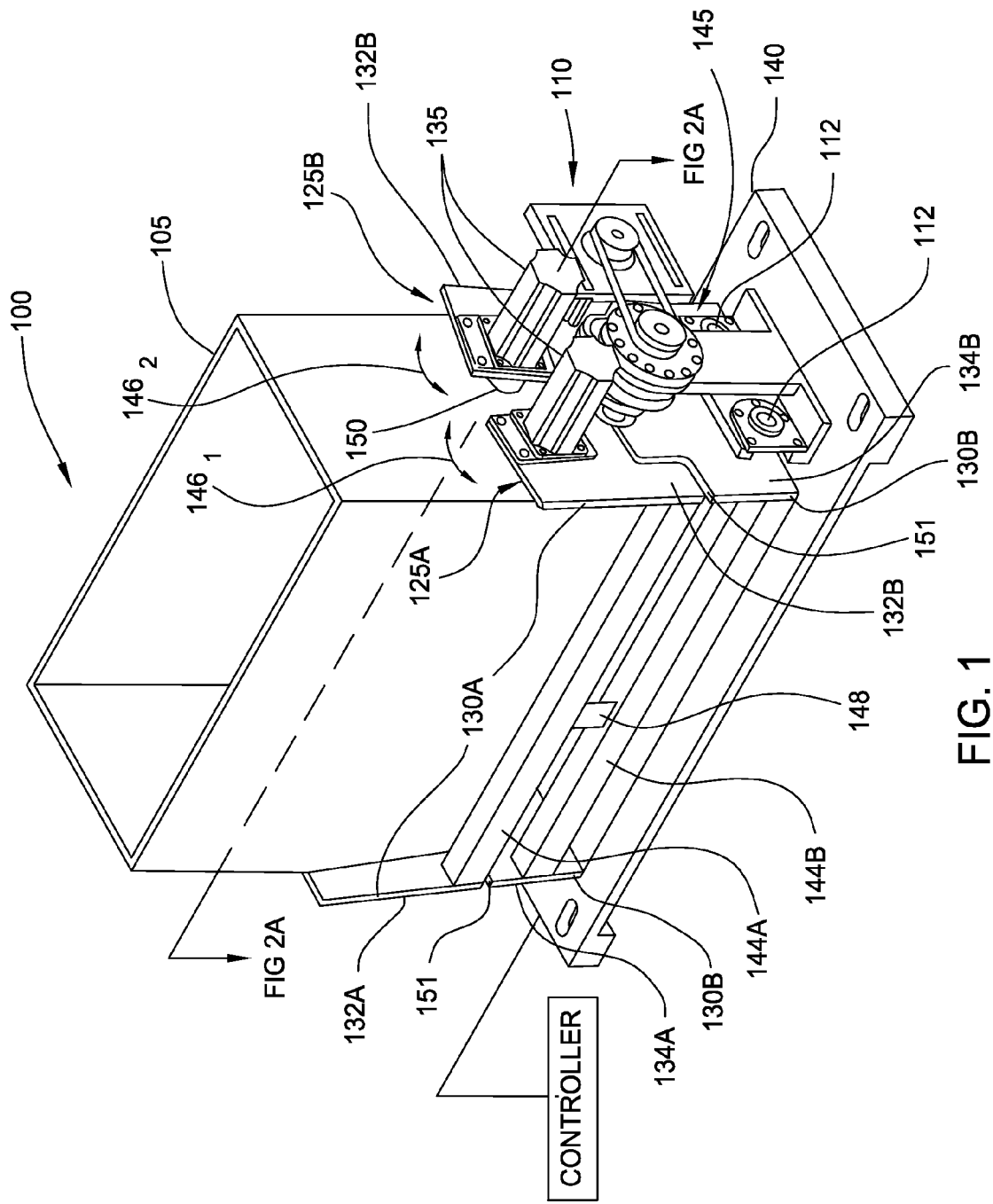
FIG. 1 is an isometric view of one embodiment of a brush box that may be utilized in a cleaning module.

FIG. 1 is an isometric view of a brush box 100 that may be utilized in a cleaning module as described above. The brush box 100 includes a tank 105 that is at least partially encased in a first bracket assembly 125A and a second bracket assembly 125B. Each of the bracket assemblies 125A, 125B are coupled to a linkage 110 that is external to (i.e., outside of) the tank 105 of the brush box 100. Each of the bracket assemblies 125A, 125B are adapted to support an actuator 135. Each actuator 135 is coupled to a cylindrical roller 115, 120 (shown in FIG. 2A) located inside the tank 105. In this embodiment, each of the cylindrical rollers 115, 120 are configured as a brush for use in a substrate cleaning process. The actuators 135 provide rotational movement of the respective cylindrical rollers 115, 120 about separate rotational axes. Each of the actuators 135 may be drive motors, such as direct drive servo motors adapted to rotate the respective cylindrical rollers 115, 120. Each of the actuators 135 are coupled to a controller adapted to control the rotational speed of the cylindrical rollers 115, 120.

A linkage 110 is coupled to each of the bracket assemblies 125A, 125B, a base 140, and an actuator 145. The linkage 110 is utilized for convenient and accurate actuation/movement of the bracket assemblies 125A, 125B. The actuator 145 is coupled to a controller to control the movement of the linkage 110.

Each of the first and second bracket assemblies 125A, 125B are coupled to the base 140 by a pivot point 112 to which the first and second bracket assemblies 125A, 125B may be adapted to pivot (upward and inward toward one another, and/or downward and outward away from one another). The movement of the first and second bracket assemblies 125A, 125B moves the cylindrical rollers 115, 120 (shown in FIG. 2A) to and away from major surfaces of a substrate.

Additionally, clearance holes (not shown) may be formed in the tank 105 to achieve rotational coupling between the brushes 115, 120, actuators 135 and the supports 125, 130. A compliant coupling element 150, such as a flexible gasket, a washer, a seal or a bellows, may be disposed around each hole and mounted between the tank 105 and the bracket assemblies 125A, 125B. Such an arrangement (1) permits relative motion of the cylindrical rollers 115, 120 relative to the walls of the tank 105; (2) protects the substrate 101 against particulate contamination that might otherwise pass into the interior of the tank 105 through the holes in the tank walls; and/or (3) permits a fluid level in the tank 105 to reach or exceed the level of the holes while preventing fluid from draining therethrough.

Figure 2A:
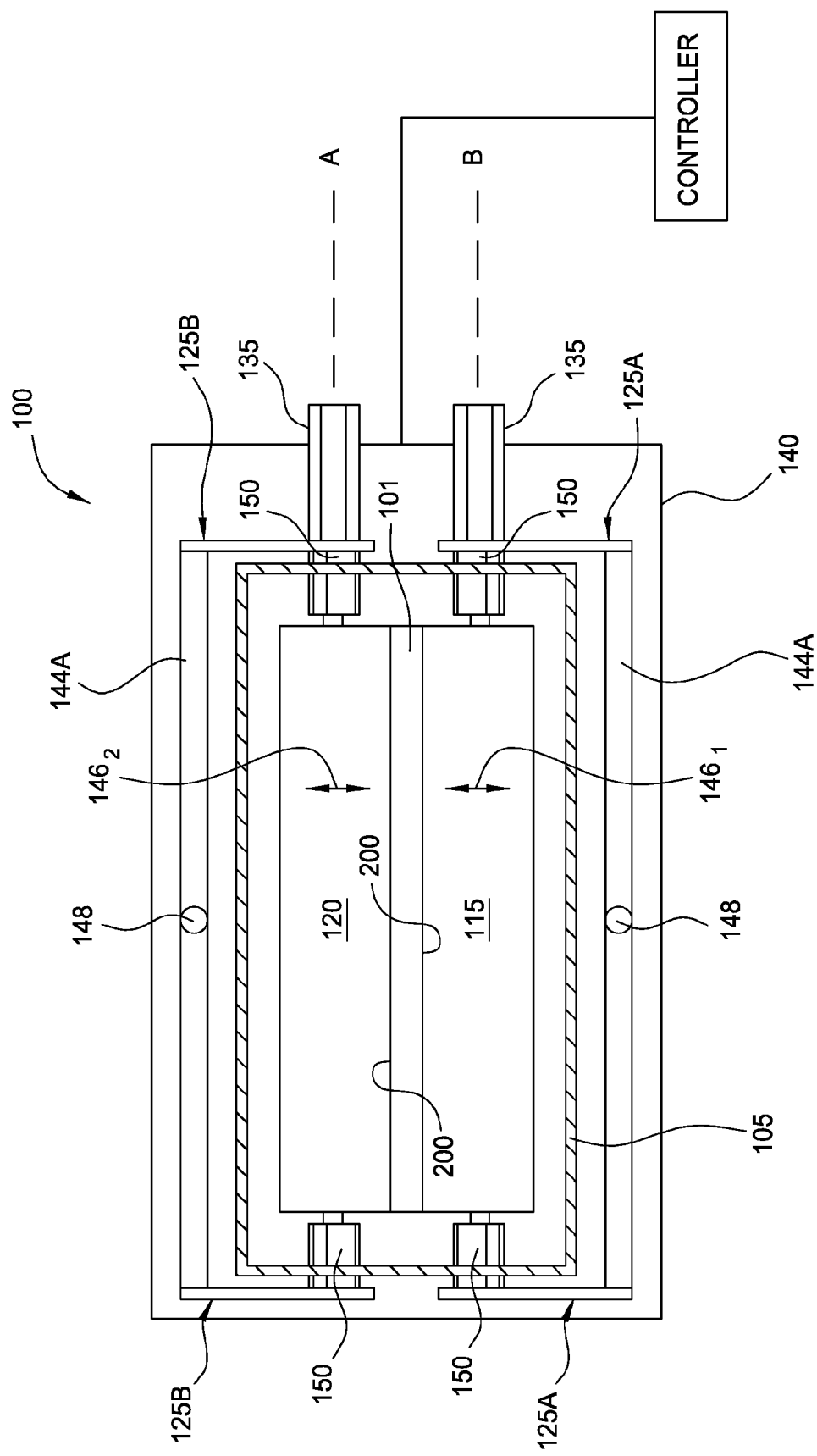
FIG. 2A is a top view of the brush box of FIG. 1 showing the cylindrical rollers in a processing position.

In operation, the first and second bracket assemblies 125A, 125B may be moved simultaneously relative to the base 140 through respective arcs $146_1$, $146_2$, as shown in FIG. 1. Such movement may cause the first and second cylindrical rollers 115, 120 to move against major surfaces 200 of the substrate 101 as shown in FIG. 2A, or to cause the first and second cylindrical rollers 115, 120 to be spaced apart (shown in FIG. 2B) to allow insertion and/or removal of the substrate 101 from the brush box 100. Although not shown, the first and second bracket assemblies 125A, 125B may be moved relative to the base 140 in a linear motion.

Each of the bracket assemblies 125A, 125B (125B is partially hidden in FIG. 1) include at least two bracket sections, shown as an upper or first bracket section 130A and a lower or second bracket section 130B. The first bracket section 130A includes a first structural support member 144A that mechanically and/or structurally couples a first side 132A and a second side 132B of the first bracket section 130A. Likewise, the second bracket section 130B includes a second structural support member 144B that mechanically and/or structurally couples a first side 134A and a second side 134B of the second bracket section 130B. Each of the first and second support members 144A, 144B may be a rigid bar or tubular member that is fastened or welded to the respective sides 132A, 134A, 132B and 134B. An alignment member 148 is coupled between each of the first and second support members 144A, 144B. In one embodiment, the alignment member 148 facilitates pivotal movement between the first and second support members 144A, 144B. While not completely shown in FIG. 1, the bracket assembly 125B may be constructed in the mirror image of the bracket assembly 125A in one embodiment. Alternatively, only one of the bracket assemblies 125A, 125B may include an alignment member 148.

In this embodiment, each of the bracket sections 130A, 130B are coupled to each other in a manner that provides unified movement of the bracket assembly 125A in the arc $146_1$, but also provides relative movement between each bracket section 130A, 130B. The alignment member 148 includes a spring mechanism or biasing device adapted to maintain mechanical and/or structural integrity between the first and second support members 144A, 144B while allowing at least relative rotational movement between the bracket sections 130A and 130B. Relative rotational movement between each of the bracket sections 130A, 130B is facilitated by a gap 151 that separates each bracket section 130A, 130B and allows relative movement between each bracket section 130A, 130B. Thus, the first and second support members 144A, 144B allow the sides 132A, 134A, 132B and 134B to remain substantially parallel and move in the arc $146_1$ in a unified manner while the alignment member 148 and the gap 151 allows at least rotational or pivotal movement of at least one of the bracket sections 130A, 130B relative to the other. In embodiments where only one of the bracket assemblies 125A, 125B utilizes an alignment member 148, the bracket assembly void of the alignment member 148 may only move in the arc $146_1$ and not include the gap 151.

Figure 2B:
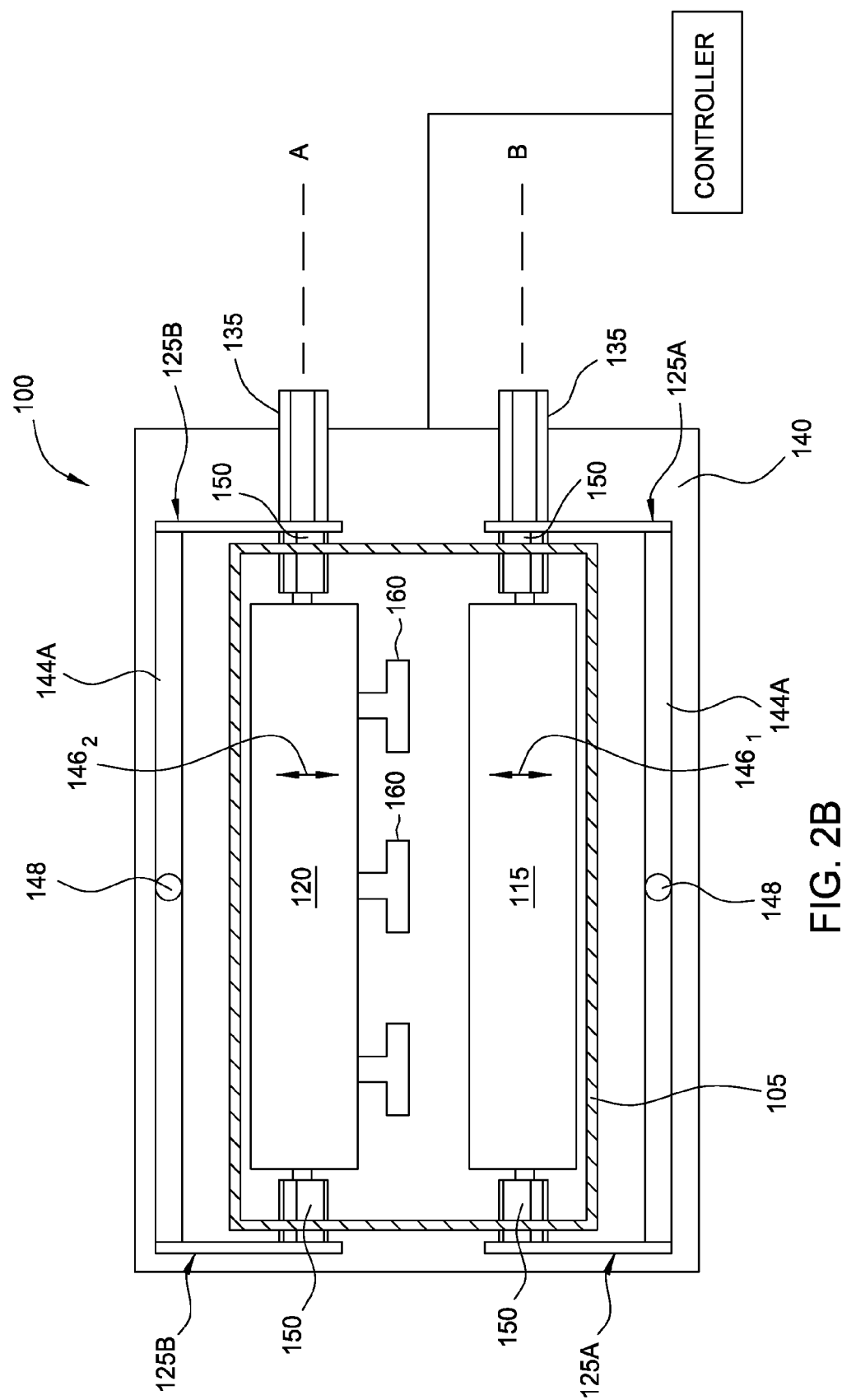
FIG. 2B is a top view of the brush box of FIG. 2A showing the cylindrical rollers in a transfer position.

FIG. 2A is a top view of the brush box 100 of FIG. 1 showing the cylindrical rollers 115, 120 in a processing position where the cylindrical rollers 115, 120 are closed or pressed against major surfaces 200 of a substrate 101. FIG. 2B is a top view of the brush box 100 of FIG. 2A in a transfer position where the cylindrical rollers 115, 120 are spaced apart to facilitate transfer of the substrate.

In operation, with reference to FIGS. 1-2B, the bracket assemblies 125A, 125B are moved outward and away from each other along the respective arcs $146_1$, $146_2$, a to provide a gap between the first and second cylindrical rollers 115, 120, as shown in FIG. 2B. The substrate 101 is transferred into the tank 105 between the first and second cylindrical rollers 115, 120 by a robot or end effector (not shown). The brush box 100 also includes one or more roller assemblies 160 configured to support and/or engage the edge of the substrate 101 and facilitate rotation of the substrate 101 in a vertical orientation during processing in the tank 105. The robot guides the substrate 101 to a position where the substrate 101 is supported and/or seated in each roller assembly 160. When the substrate 101 is supported by the roller assemblies 160, the robot may be removed from the tank 105.

While the substrate 101 is supported by the roller assemblies 160, the bracket assemblies 125A, 125B are moved inward and toward each other and the first and second cylindrical rollers 115, 120 contact the major surfaces 200 of the substrate 101. The one or more of the roller assemblies 160 are coupled to an actuator (not shown) that rotates the respective roller assembly 160 which causes the substrate 101 to rotate in axis C (FIG. 3). The first and second cylindrical rollers 115, 120 are caused to rotate about axes A and B while the substrate 101 is rotated in axis C to clean the substrate 101. In one embodiment, axes A and B are substantially parallel while axis C is substantially perpendicular to axes A and B.

During the cleaning process, an outer surface of each of the cylindrical rollers 115, 120 contacts the major surfaces 200 of the substrate 101. In one embodiment, the outer surface of each of the cylindrical rollers 115, 120 may be made of or include a flexible and/or compressible polymeric material, such as a foam material, for example polyvinyl alcohol (PVA) or polyurethane foam, or other foam or compressible material suitable for cleaning the substrate.

Uniform contact and consistent pressure between each of the cylindrical rollers 115, 120 and the major surfaces 200 of the substrate 101 is desired during the cleaning process. The uniform contact and consistent pressure provides efficient cleaning of the substrate 101 by providing sufficient friction and/or contact between the cylindrical rollers 115, 120 and the substrate 101. The friction and/or contact between the cylindrical rollers 115, 120 and the substrate 101 additionally provides rotational speed control of the substrate 101.

It is preferred that the diameter running along the length of the outer surface of each of the cylindrical rollers 115, 120 is of a substantially uniform or equal diameter. However, the compressible material of the cylindrical rollers 115, 120 may be deformed such that the outer diameter is not uniform and/or the outer surface includes flat spots. The uneven area or flat spots in the outer surface may be caused by improper handling of the cylindrical rollers 115, 120 prior to or during installation. Flat or uneven areas disposed on the surface of the cylindrical rollers 115, 120 cause less than full contact between the cylindrical rollers 115, 120 and the substrate 101. The flat or uneven areas of the cylindrical rollers 115, 120 exerts less pressure on the substrate 101 and may cause a portion of the cylindrical rollers 115, 120 to lose contact with the substrate 101 entirely. The reduced pressure and/or contact reduces friction between the cylindrical rollers 115, 120. The reduced friction minimizes cleaning efficiency and may additionally allow the substrate 101 to rotate faster or slower than desired. The rotational speed of the substrate 101 may trip an overspeed or underspeed alarm, which may put the brush box 100 out of service until the problem is determined and addressed. Both of the reduced cleaning efficiency and the problems associated with substrate overspeed/underspeed reduces throughput.

After the substrate 101 has been cleaned by the first and second cylindrical rollers 115, 120, the rotation of the first and second cylindrical rollers 115, 120 and the substrate 101 may be stopped. The bracket assemblies 125A, 125B are moved outward and away from each other to provide a gap between the first and second cylindrical rollers 115, 120 to allow the substrate 101 to be removed from the tank 105 by the robot or end effector. After the substrate 101 is removed, another substrate may be transferred into the tank 105 for cleaning.

FIG. 3 is an isometric view of one embodiment of a bracket assembly 125A that may be utilized in the brush box 100 of FIGS. 1-2B. Each of the bracket sections 130A, 130B are coupled to each other in a manner that provides unified rotational movement of the bracket assembly 125A in an arc indicated by the arrow at 305 in order to move the cylindrical roller 115 towards and away from a substrate (not shown). The direction indicated by the arrow at 305 is the same as the arc 146$_2$ shown in FIG. 1. During operation, the cylindrical roller 115 rotates about axis B while the substrate 101 is rotated in axis C. In one embodiment, axis C is substantially perpendicular to axis B.

Each of the bracket sections 130A, 130B are coupled to respective structural support members 144A, 144B. Each structural support member 144A, 144B is fastened, welded, or otherwise joined to the respective sides 132A, 132B, 134A, and 134B. The first structural support member 144A is coupled between the sides 132A and 132B in a manner that maintains rigidity and spacing between the sides 132A and 132B. Likewise, the second structural support member 144B is coupled between sides 134A and 134B in a manner that maintains rigidity and spacing between the sides 132A and 132B. In one embodiment, the first structural support member 144A and the second structural support member 144B maintains the respective sides 132A, 132B, 134A, and 134B in a substantially parallel relationship. In another embodiment, the longitudinal axes of the cylindrical roller 115 and the first structural support member 144A are substantially parallel. The parallel relationship between the cylindrical roller 115 and the first structural support member 144A is maintained by the rigid connection between the first structural support member 144A and the sides 132A and 132B.

In one embodiment, the alignment member 148 provides potential energy that facilitates movement of one or both of the sides 132A and 132B in the direction 310. The cylindrical roller 115 is coupled between the sides 132A and 132B and moves with the sides 132A and 132B in the direction 310. For example, the alignment member 148 is coupled to each of the first structural support member 144A and the second structural support member 144B in a manner that allows rotation of the first structural support member 144A and the second structural support member 144B about a rotational axis $A_R$. In this example, the alignment member 148 also allows the first structural support member 144A to pivot about pivotal axis $A_P$ relative to the second structural support member 144B.

In operation, the bracket section 130B is coupled to the pivot point 112 that facilitates movement of the bracket assembly 125B in the arc 305. In one embodiment, a normal operation consists of the longitudinal axes of the cylindrical roller 115 (which may be the same as the rotational axis A") and the first structural support member 144A being substantially parallel with the longitudinal axis of the second structural support member 144B. In this embodiment, the longitudinal axis of the cylindrical roller 115 is generally parallel with the plane of a substrate (not shown). The alignment member 148 is coupled between the first and second structural support members 144A, 144B and allows movement of the bracket section 130A relative to the bracket section 130B in the direction indicated at 310. Thus, in one embodiment, the alignment member 148 allows the longitudinal axes of one or both of the cylindrical roller 115 and the first structural support member 144A to move out of a parallel relationship with the second structural support member 144B. The gap 151 is sized to permit slight movement of the sides 132A 132B relative to the sides 134A, 134B as the bracket section 130A rotates or pivots relative to the bracket section 130B. In one embodiment, the gap 151 is sized to allow the sides 132A, 132B to move relative to the sides 134A, 134B, respectively, in a dimension in at least the Y direction between about 1 mm to about 5 mm, for example, about 3 mm.

In some embodiments, only one of the bracket assemblies 125A, 125B includes an alignment member 148, two discrete bracket sections, such as bracket sections 130A, 130B, and/or a gap 151. In this embodiment, only one of the bracket assemblies 125A or 125B is provided with rotation in axis $A_P$. In other embodiments, both of the bracket assemblies 125A, 125B are provided with an alignment member 148, two discrete bracket sections 130A, 130B and the gap 151. However, movement in axis $A_P$ may be optional in this embodiment. For example, the bracket sections 130A and 130E may be fastened to each other to prevent or minimize movement in axis $A_P$. In one embodiment (not shown), a structural member, such as piece of strap, angle or channel may be coupled between the bracket sections 130A and 130B by fasteners to prevent or minimize movement in axis $A_P$.

FIG. 4 is a cross-sectional view of one embodiment of an alignment member 148. The alignment member 148 includes a central shaft 405 that is coupled between the first structural support member 144A and the second structural support member 144B. The second structural support member 144B includes a base 410 having a channel 420 that receives a first end 415 of the central shaft 405. A fastener 425, such as a bolt or screw, secures the central shaft 405 to the base 410.

A second end 430 of the central shaft 405 is coupled to the first structural support member 144A in a manner that allows the first structural support member 144A to pivot relative to the central shaft 405 and the second structural support member 144B. The second end 430 of the central shaft 405 is coupled to a pivot mechanism 435 disposed in an opening 440 formed in the first structural support member 144A.

The pivot mechanism 435 includes a first bearing assembly 445A and a second bearing assembly 445B separated by a spacer 450. The first bearing assembly 445A is retained on the central shaft 405 by an annular shoulder 465 formed on the central shaft 405. The second bearing assembly 455B is retained on the central shaft 405 by a nut 470 that, in one embodiment, is threadedly connected to the central shaft 405. The spacer 450 is adapted to contact a race of each of the first bearing assembly 445A and second bearing assembly 445B. The pivot mechanism 435 is covered by a cap 475 that may be fastened to the first structural support member 144A.

In one embodiment, the pivot mechanism 435 is a preloaded bearing. In this embodiment, the first bearing assembly 445A includes a spring form 455 that is in contact with at least a portion of the first bearing assembly 445A and a shoulder region 460 formed on a wall of the opening 440. In one embodiment, the spring form 455 is a compression spring, such as a flat wire compression spring or a wave spring. In this manner, the spring form 455 exerts a force between the first bearing assembly 445A and the shoulder region 460 to pre-load at least the first bearing assembly 445A relative to the first structural support member 144A. In one example, the spring form 455 is a wave spring available from Smalley Steel Ring Co., of Lake Zurich, Ill.

Figure 5A:
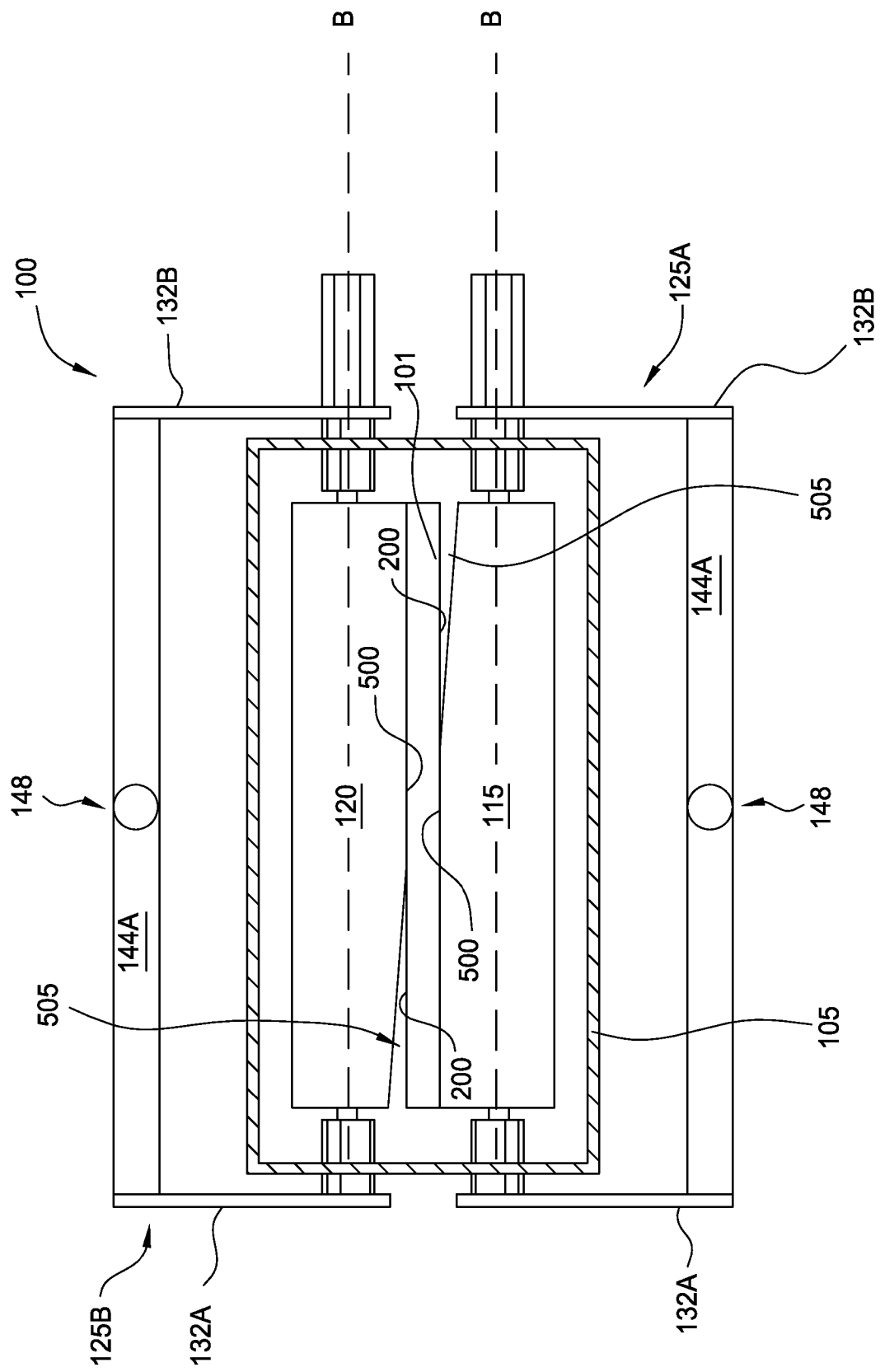
FIG. 5A is a schematic top view of a brush box having one embodiment of an alignment member coupled to two bracket assemblies.

FIG. 5A is a schematic top view of a brush box 100 having an alignment member 148 as described herein. In operation, the alignment member 148 would operate to cause an outer surface 500 of the cylindrical rollers 115, 120 to be in full contact with the major surfaces of the substrate 101. However, the alignment member 148 is not activated in this embodiment for sake of explanation. The outer surface 500 of each of the cylindrical rollers 115, 120 include a flat spot 505, which may be defined as an area on the outer surface 500 of the respective cylindrical rollers 115, 120 that is not round or is less than the average outer diameter of the outer surface 500 of the cylindrical rollers 115, 120. The flat spot 505 may be caused by improper handling of the cylindrical rollers 115, 120 prior to or during installation. While a flat spot 505 is shown on both of the cylindrical rollers 115, 120, the flat spot 505 may be formed on only one of the cylindrical rollers 115, 120 and/or in different portions of the cylindrical rollers 115, 120.

In this embodiment, a first orientational axis B of the cylindrical rollers 115, 120 is substantially parallel to a plane defined by one or both of the major surfaces 200 of the substrate 101. In the conventional systems, the flat spot will not contact the substrate as the rollers are not capable of movement out of the orientation of the axis B. As a result, the flat spot in conventional systems cause less than full contact between the rollers and the substrate, which lead to inefficient cleaning of the substrate and/or cause an overspeed or underspeed situation.

Figure 5B:
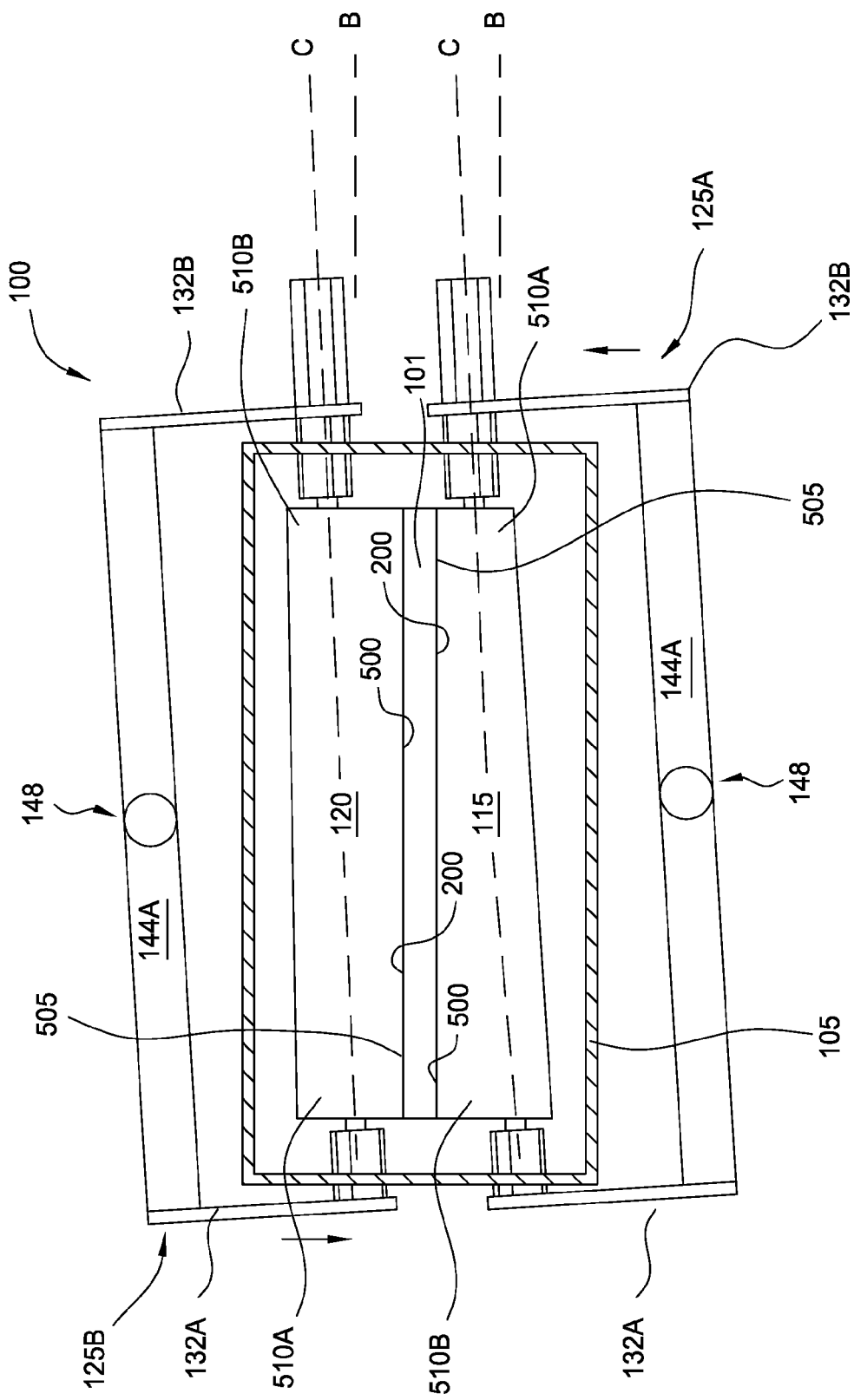
FIG. 5B is a schematic top view of a brush box showing the alignment member of FIG. 5A in an actuated position.

FIG. 5B is a schematic top view of a brush box 100 showing the alignment members 148 activated in order to provide corrective action that allows full contact between the substrate 101 and the outer surface 500 of the cylindrical rollers 115, 120. In this embodiment, each of the cylindrical rollers 115, 120 include a first end 510A and a second end 510B and full contact between the outer surface 500 of the cylindrical rollers 115, 120 against the substrate 101 is provided between the first and second ends 510A, 510B. The alignment member 148 allows the first structural support members 144A to pivot the axis B of the cylindrical rollers 115, 120 to a second orientational axis C. In one aspect, the orientational axes B and C are longitudinal axes and/or rotational axes of the cylindrical rollers 115, 120, such as axis A" (FIG. 3) and/or axis A' (FIGS. 2A, 2B), wherein the orientation of the longitudinal and/or rotational axis is pivoted or otherwise in a different orientation relative to the substrate 101 and/or the second structural support member 144B. In one embodiment, the second axis C is angled relative to the first axis B such that the two axes are not parallel. In one embodiment, each of the first end 510A and second end 510B of the cylindrical rollers 115, 120 are urged against the substrate 101 with a substantially equal pressure. Thus, full contact between the substrate 101 and the cylindrical rollers 115, 120 is maintained as the flat spot 505 is encountered.

Figure 5C:
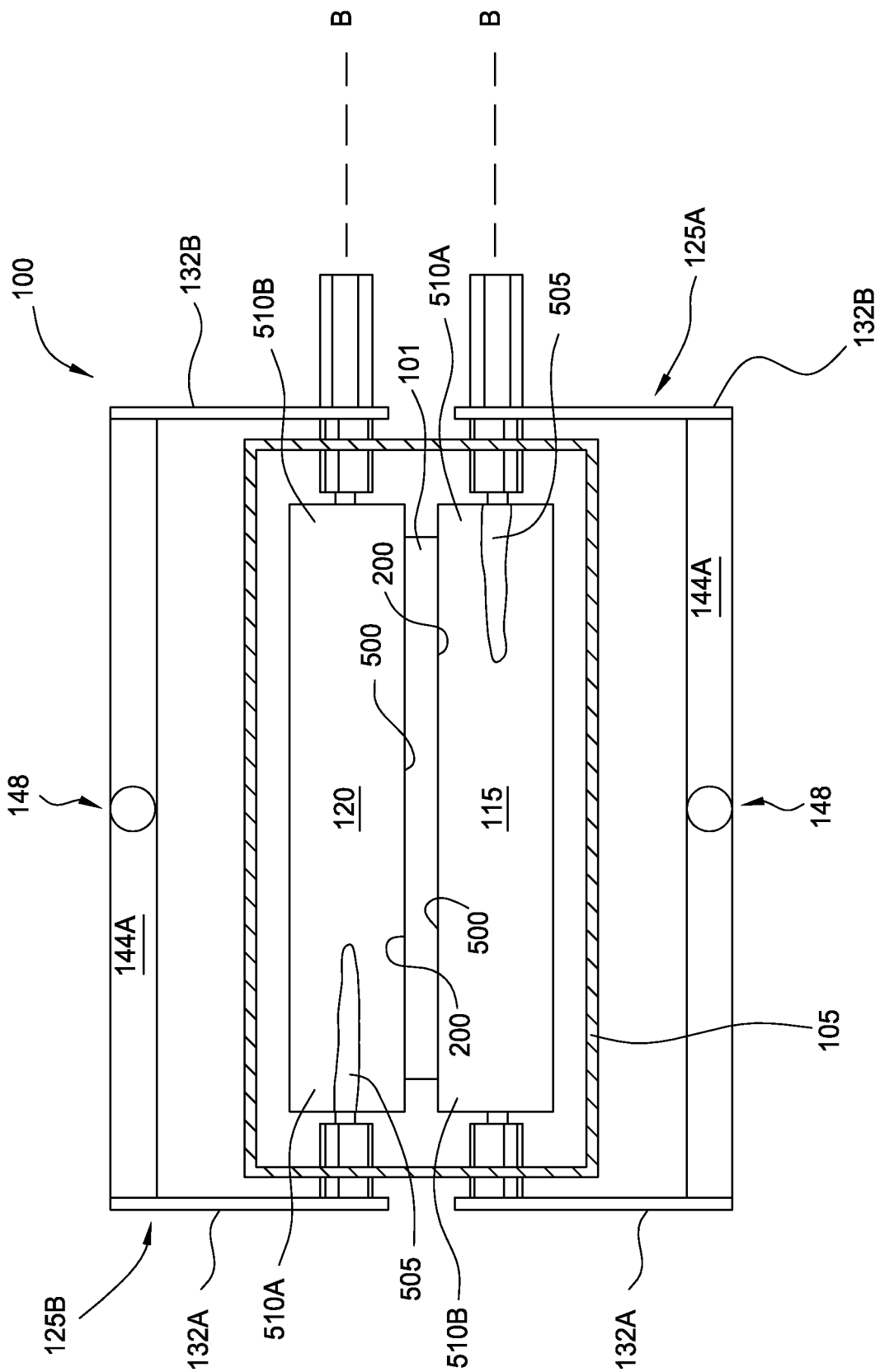
FIG. 5C is a top view of the brush box of FIG. 5B showing the continued rotation of the cylindrical rollers.

FIG. 5C is a top view of the brush box 100 of FIG. 5B showing the continued rotation of the cylindrical rollers 115, 120. The cylindrical rollers 115, 120 rotate past the flat spot 505 and the cylindrical rollers 115, 120 are returned to the orientational axis B. As the cylindrical rollers 115, 120 continue rotation and the flat spot 505 is adjacent the substrate 101, the alignment members 148 allow rotation of the cylindrical rollers 115, 120 to move the entire outer surface 500 of the cylindrical rollers 115, 120 against the substrate 101 as shown in FIG. 5B. The operation of the alignment members 148 may continue during repeated rotation of the cylindrical rollers 115, 120 as shown in FIGS. 5B and 5C until the cleaning process is completed.

In one embodiment, the first orientational axis B is parallel with the plane of the major surfaces 200 of the substrate 101 during normal operation of the brush box 100. In another embodiment, the first orientational axis B angled relative to the plane of the major surfaces 200 of the substrate 101 during normal operation of the brush box 100. In this example, the alignment members 148 may promote full contact of the cylindrical rollers 115, 120 with the substrate 101 in an angled relationship relative to the plane of the major surfaces 200 of the substrate 101 during at least a portion of the cleaning process.

In another embodiment, when the cylindrical rollers 115, 120 are initially urged against the substrate 101, the alignment members 148 may adjust the orientation of axis B relative to the plane of the major surfaces 200 of the substrate 101 prior to or during the primary revolution of the cylindrical rollers 115, 120. For example, one or both of the first ends 510A may initially contact the substrate 101 based on the movement of the linkage 110 (FIG. 1). After the initial contact between the first ends 510A and the substrate 101, the alignment members 148 provide rotational movement to provide contact between the second end 510B of the cylindrical rollers 115, 120 and the substrate 101. In this example, the alignment action provided by the alignment members 148 may be performed prior to or during initial rotational movement of the cylindrical rollers 115, 120.

In one aspect, the cylindrical rollers 115, 120 are floating relative to the plane of the substrate 101 and when a flat spot 505 or other uneven portion of the outer surface 500 of one or both of the cylindrical rollers 115, 120 is encountered, the alignment member 148 adjusts the respective cylindrical roller 115, 120 to provide substantially full, consistent contact between the substrate 101 and the outer surface 500.

Figure 6:
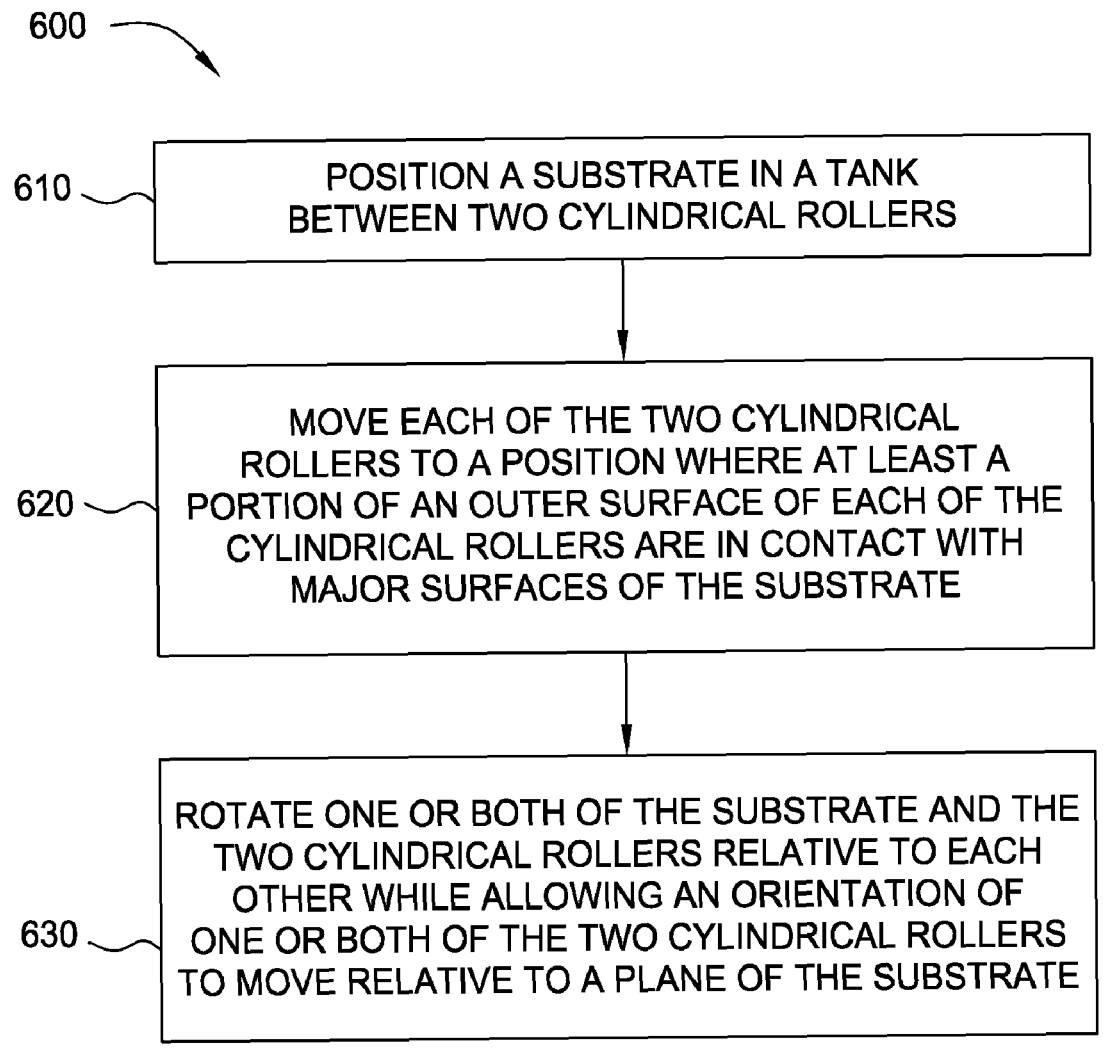
FIG. 6 is a flowchart showing one embodiment of a method 600 that may be utilized with the brush box of FIG. 1.

FIG. 6 is a flowchart showing one embodiment of a method 600 that may be utilized with the brush box 100. At 610, a substrate 101 is transferred to a tank 105 having two cylindrical rollers 115, 120 disposed therein. The substrate 101 is positioned between the cylindrical rollers 115, 120 disposed in the tank 105. At 620, each of the two cylindrical rollers 115, 120 are moved to a position within the tank 105 where at least a portion of an outer surface 500 of each of the cylindrical rollers 115, 120 are in contact with the major surfaces 200 of the substrate 101. For example, the linkage 110 is activated to move the bracket assemblies 125A, 125B inward and toward each other to cause contact between the outer surface 500 of the cylindrical rollers 115, 120 and the substrate 101.

At 630, one or both of the substrate 101 and the cylindrical rollers 115. 120 are rotated relative to each other to clean the substrate 101. During the relative rotation of the substrate 101 and the cylindrical rollers 115, 120, a first orientational axis B of the respective cylindrical rollers 115, 120 is floating or allowed to move relative to a plane of the substrate 101. In the case where a flat spot 505 or other uneven portion of the outer surface 500 of one or both of the cylindrical rollers 115, 120 is encountered, the orientational axis B is allowed to move to a second orientational axis C relative to the plane of the major surfaces 200 of the substrate 101. Thus, substantially consistent contact between the outer surface 500 of the cylindrical rollers 115, 120 is maintained at all times during each revolution of the cylindrical rollers 115, 120.

While the foregoing is directed to embodiments of the invention, other and further embodiments of the invention may be devised without departing from the basic scope thereof.

What is claimed is:

1. A brush box for processing a semiconductor substrate, comprising:
   a base;
   a tank disposed on the base; and
   a pair of bracket assemblies disposed on opposing sides of the tank and movably coupled to the base, at least one of the bracket assemblies comprising:
      a first bracket section having a first side and a second side separated by a first structural support member; and
      a second bracket section having a first side and a second side separated by a second structural support member, first bracket section being fixed to the second bracket section for lateral movement of the respective bracket assembly relative to the base, and the first bracket section being pivotally movable relative to the second bracket section, wherein the first structural support member and second structural support member are coupled together by an alignment member that provides common movement of both of the structural support members about a rotational axis and movement of the first structural support member in a pivotal axis relative to the second structural support member.

2. The brush box of claim 1, wherein the alignment member further comprises:
   a shaft between the first structural support member and the second structural support member.

3. The brush box of claim 2, wherein the shaft is disposed in a channel formed in the second structural support member.

4. The brush box of claim 1, wherein the alignment member further comprises:
   a pivot mechanism at least partially disposed in an opening formed in the first structural support member.

5. The brush box of claim 4, wherein the pivot mechanism comprises a shaft and a preloaded first bearing assembly coupled between the shaft and the first structural support member.

6. The brush box of claim 5, wherein the preloaded first bearing assembly includes a wave spring coupled between a shoulder formed on the opening and the first bearing assembly.

7. The brush box of claim 6, wherein the pivot mechanism further comprises a second bearing assembly spaced apart from the first bearing assembly by a sleeve.

8. A brush box for processing a semiconductor substrate, comprising:
   a base;
   a tank disposed on the base;
   a pair of bracket assemblies disposed on opposing sides of the base and being coupled to an actuator providing movement of each bracket assembly in a rotational axis relative to the base, at least one of the bracket assemblies comprising:
      a first bracket section hingedly coupled to the base; and
      a second bracket section having a cylindrical roller coupled thereto, the second bracket section being fixed to the first bracket section for movement with the first bracket section on the rotational axis, and the second bracket section being movable in a pivotal axis relative to the first bracket section, wherein the first bracket sections and the second bracket sections include a first structural support member and a second structural support member, respectively, coupled between opposing sides of the first bracket sections and second bracket sections; and
   an alignment member disposed between the first structural support member and the second structural support member, the alignment member comprising a central shaft disposed between the first structural support member and the second structural support member, wherein the central shaft is disposed in a channel formed in the second structural support member.

9. The brush box of claim 8, wherein the alignment member further comprises:
   a pivot mechanism at least partially disposed in an opening formed in the first structural support member.

10. The brush box of claim 9, wherein the pivot mechanism comprises a preloaded bearing assembly coupled between the central shaft and the first structural support member.

11. A brush box for processing a semiconductor substrate, comprising:
   a base;
   a tank disposed on the base; and
   a pair of bracket assemblies disposed on opposing sides of the tank and movably coupled to the base, at least one of the bracket assemblies comprising:

a first bracket section having a first side and a second side separated by a first structural support member; and a second bracket section having a first side and a second side separated by a second structural support member, first bracket section being fixed to the second bracket section for lateral movement of the respective bracket assembly relative to the base, and the first bracket section being pivotally movable relative to the second bracket section, wherein the first structural support member and second structural support member are coupled together by an alignment member that provides common movement of both of the structural support members about a rotational axis and movement of the first structural support member in a pivotal axis relative to the second structural support member.

12. The brush box of claim 11, wherein the alignment member further comprises:

a shaft between the first structural member and the second structural member.

13. The brush box of claim 12, wherein the shaft is disposed in a channel formed in the second structural support member.

14. The brush box of claim 11, wherein the alignment member further comprises:

a pivot mechanism at least partially disposed in an opening formed in the first structural support member.

15. The brush box of claim 14, wherein the pivot mechanism comprises a shaft and a preloaded first bearing assembly coupled between the shaft and the first structural support member.

16. The brush box of claim 15, wherein the preloaded first bearing assembly includes a wave spring coupled between a shoulder formed on the opening and the first bearing assembly.

17. The brush box of claim 16, wherein the pivot mechanism further comprises a second bearing assembly spaced apart from the first bearing assembly by a sleeve.

* * * * *